US011305113B2

(12) United States Patent
Toong

(10) Patent No.: US 11,305,113 B2
(45) Date of Patent: Apr. 19, 2022

(54) NOCTURIA REDUCTION SYSTEM

(71) Applicant: Neurostim Solutions LLC, Waltham, MA (US)

(72) Inventor: Hoo-Min D. Toong, Cambridge, MA (US)

(73) Assignee: NEUROSTIM SOLUTIONS LLC, Waltham, MA (US)

( * ) Notice: Subject to any disclaimer, the term of this patent is extended or adjusted under 35 U.S.C. 154(b) by 63 days.

(21) Appl. No.: 16/142,258

(22) Filed: Sep. 26, 2018

(65) Prior Publication Data

US 2019/0143108 A1    May 16, 2019

Related U.S. Application Data

(60) Provisional application No. 62/590,829, filed on Nov. 27, 2017, provisional application No. 62/584,790, filed on Nov. 11, 2017.

(51) Int. Cl.
| | |
|---|---|
| *A61N 1/36* | (2006.01) |
| *A61N 1/04* | (2006.01) |
| *A61B 8/08* | (2006.01) |
| *A61B 8/00* | (2006.01) |
| *A61B 5/00* | (2006.01) |
| *A61B 5/20* | (2006.01) |

(52) U.S. Cl.
CPC ............ *A61N 1/36007* (2013.01); *A61B 8/08* (2013.01); *A61B 8/4227* (2013.01); *A61B 8/5223* (2013.01); *A61N 1/0492* (2013.01); *A61N 1/36031* (2017.08); *A61B 5/204* (2013.01); *A61B 5/4812* (2013.01); *A61B 5/7264* (2013.01)

(58) Field of Classification Search
CPC ... A61B 5/7246; A61B 5/0402; A61B 5/0408; A61B 5/7264; A61B 5/7267; G16H 50/50; G16H 50/70; G16H 50/20; G16H 30/20; G16H 70/20; G01N 21/359
See application file for complete search history.

(56) References Cited

U.S. PATENT DOCUMENTS

| | | |
|---|---|---|
| 7,643,874 B2 | 1/2010 | Nitzan et al. |
| 7,689,285 B2 | 3/2010 | Garabet |
| 7,922,676 B2 | 4/2011 | Daskal et al. |
| 9,855,427 B2 | 1/2018 | Bennett et al. |
| 10,342,977 B2 | 7/2019 | Raghunathan |

(Continued)

FOREIGN PATENT DOCUMENTS

| | | |
|---|---|---|
| JP | 2016093209 A | 5/2016 |
| JP | 2017533024 A | 11/2017 |

(Continued)

OTHER PUBLICATIONS

Yogi A. Patel; Kilohertz Electrical Stimulation Nerve Conduction Block: Effects of Electrode Surface Area; IEEE Transactions On Neural Systems and Rehabilitation Engineering, vol. 25, No. 10, Oct. 2017.

*Primary Examiner* — Ankit D Tejani
*Assistant Examiner* — Joshua Brendon Solomon
(74) *Attorney, Agent, or Firm* — Potomac Law Group, PLLC

(57) ABSTRACT

Example inventions reduce nocturia for a user. Examples determine that the user is sleeping, determine that the user has an urge to urinate, and then apply external electrical stimulation to a tibial nerve of the user.

22 Claims, 13 Drawing Sheets

(56) References Cited

U.S. PATENT DOCUMENTS

| | | | |
|---|---|---|---|
| 2002/0019652 A1 | 2/2002 | Silva et al. | |
| 2004/0054008 A1 | 3/2004 | Araki | |
| 2008/0300449 A1 | 12/2008 | Gerber et al. | |
| 2009/0132018 A1 | 5/2009 | DiUbaldi et al. | |
| 2009/0192556 A1* | 7/2009 | Wu | A61B 5/0031 607/3 |
| 2010/0181934 A1* | 7/2010 | Chidester | H05B 47/11 315/307 |
| 2012/0143107 A1 | 6/2012 | Henley | |
| 2013/0110064 A1 | 5/2013 | Richardson et al. | |
| 2014/0018636 A1* | 1/2014 | Contant | A61B 5/686 600/301 |
| 2014/0121473 A1 | 5/2014 | Banet et al. | |
| 2014/0194951 A1 | 7/2014 | Gong et al. | |
| 2014/0324120 A1 | 10/2014 | Bogie et al. | |
| 2015/0290463 A1 | 10/2015 | Yonce | |
| 2015/0335888 A1 | 11/2015 | Demers et al. | |
| 2016/0015962 A1 | 1/2016 | Maragheh et al. | |
| 2016/0125759 A1* | 5/2016 | Dougherty | G09B 19/00 434/236 |
| 2016/0263376 A1 | 9/2016 | Yoo et al. | |
| 2016/0339239 A1* | 11/2016 | Yoo | A61N 1/3606 |
| 2017/0001003 A1 | 1/2017 | Pivonka et al. | |
| 2017/0036020 A1* | 2/2017 | Harrah | A61N 1/0514 |
| 2017/0224990 A1 | 8/2017 | Goldwasser et al. | |
| 2017/0281938 A1* | 10/2017 | Creasey | A61B 8/08 |
| 2017/0293846 A1 | 10/2017 | Zyglowicz et al. | |
| 2017/0333695 A1 | 11/2017 | Kaplan et al. | |
| 2018/0116877 A1 | 5/2018 | Ineichen | |
| 2018/0133479 A1 | 5/2018 | Bennett et al. | |
| 2018/0318585 A1 | 11/2018 | Pfeifer | |
| 2019/0001129 A1* | 1/2019 | Rosenbluth | A61N 1/36014 |
| 2019/0001135 A1* | 1/2019 | Yoo | A61N 1/36142 |
| 2020/0069941 A1 | 3/2020 | Campean et al. | |
| 2020/0069942 A1 | 3/2020 | Campean et al. | |

FOREIGN PATENT DOCUMENTS

| | | |
|---|---|---|
| WO | 2009064641 A1 | 5/2009 |
| WO | 2015183620 A3 | 4/2016 |
| WO | 2017132067 A2 | 8/2017 |
| WO | 2017180661 A1 | 10/2017 |

* cited by examiner

NOCTURIA REDUCTION SYSTEM

CROSS REFERENCE TO RELATED APPLICATIONS

This application claims priority to U.S. Provisional Patent Application Ser. No. 62/584,790, filed on Nov. 11, 2017, and to U.S. Provisional Patent Application Ser. No. 62/590,829, filed on Nov. 27, 2017. The disclosure of each of these applications is hereby incorporated by reference.

FIELD

The invention is directed generally to improving bladder control to reduce the side effects of nocturia and reducing interruptions to sleep from nocturia.

BACKGROUND INFORMATION

Nocturia affects the quality of sleep and aggravates the dangers of nighttime injury, particularly among the elderly. Nocturia (or "nycturia") is the complaint that the individual has to wake at night one or more times for voiding the bladder (i.e., to urinate). Studies have shown that more than 50% of men and women over the age of 60 have been measured to have nocturia. Nocturia symptoms often worsen with age.

Nocturia affects the individual in direct and indirect ways. A direct effect is a loss of quality sleep due to the repeated waking interruptions. An indirect effect is injury due to waking and getting out of bed to use the toilet in the dark of night, and stumbling or falling on the way. This latter, indirect effect is particularly serious for old and infirm individuals, as the injuries may lead to complications or death.

DETAILED DESCRIPTION

Example inventions utilize externally positioned nerve stimulation to modify human behavior to reduce the interruptions to sleep and the incidence of nocturnal injury attributed to nocturia, by reducing the urge to urinate and deferring micturitions until a later time.

Percutaneous tibial nerve stimulation ("PTNS") is well-correlated to a reduction in the urge to urinate (the "micturition reflex"), most likely caused by the stimulated tibial nerve bundle interacting with the sacral nerve plexus to reduce the effectiveness of the sacral nerve plexus on activating the bladder detrusor muscle temporarily. This reduction in the squeezing action of the detrusor muscle reduces the urgency to urinate, which may occur in users whose bladders are holding a much smaller volume of liquid than normally needs to be voided.

In contrast, examples of the invention eschew percutaneous stimulation in favor of transcutaneous stimulation, avoiding the penetration of the skin.

Figure 1:
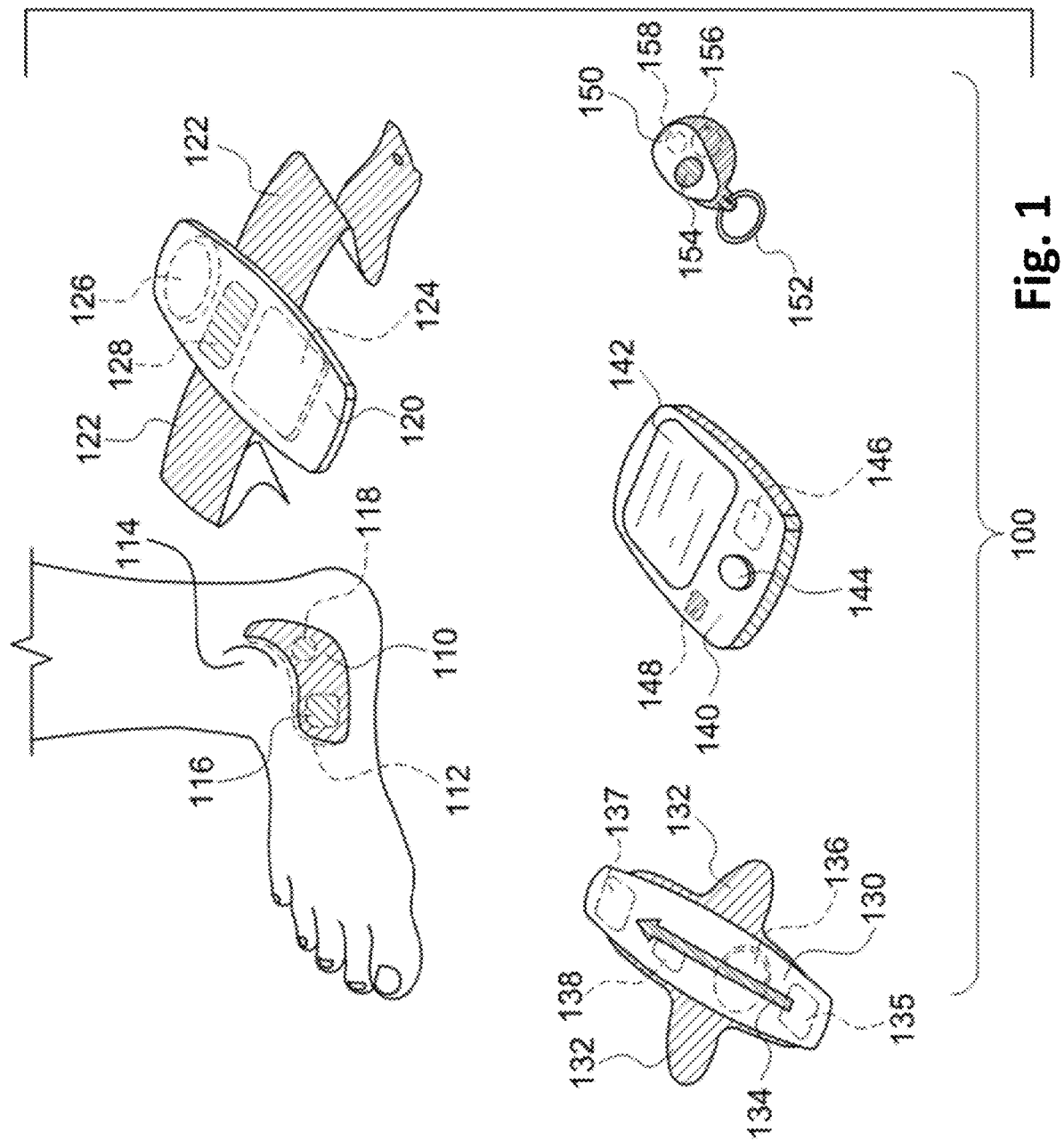
FIG. 1 illustrates an example nocturia reduction system.

FIG. 1 illustrates an example nocturia reduction system 100. System 100 includes patch 110 (also referred to a tibial Topical Nerve Stimulator/Sensor ("TNSS"), Topical Nerve Activator ("TNA") patch, smart band aid or smartpad) that includes a securing mechanism 112 adapted to secure patch 110 near a user's ankle 114, a power source 116 and a processor 118 (including instructions executed by processor 118). System 100 further includes a bladder monitoring device 120 that includes a securing mechanism 122, a bladder sensor 124, a power source 126 and a processor 128 (including instructions executed by processor 128). System 100 further includes a posture indication device 130 that includes a securing mechanism 132, an alignment mark 134, a lower detector sensor 135, a power source 136, an upper detector sensor 137 and a processor 138 (including instructions executed by processor 138). System 100 further includes a smart controller 140 with a display 142, an acknowledgment button 144, a power source 146, a microphone (not shown) and a processor 148 (including instructions executed by processor 148). System 100 further includes a fob 150 that includes a securing mechanism 152, a button 154, a power source 156, and a processor 158 (including instructions executed by processor 158).

Patch 110 includes electrodes that are oriented to be aligned with a human tibial nerve on ankle 114. Patch 110 in one example can include a flexible substrate, a malleable dermis conforming bottom surface of the substrate including adhesive and adapted to contact the dermis, a flexible top outer surface of the substrate approximately parallel to the bottom surface, electrodes positioned on the patch proximal to the bottom surface and located beneath the top outer surface and directly contacting the flexible substrate, electronic circuitry embedded in the patch and located beneath the top outer surface and integrated as a system on a chip that is directly contacting the flexible substrate, the electronic circuitry integrated as the system on the chip and including an electrical signal generator integral to the malleable dermis conforming bottom surface configured to electrically activate the electrodes, a signal activator coupled to the electrical signal generator, a nerve stimulation sensor that provides feedback in response to a stimulation of one or more nerves, an antenna configured to communicate with a remote activation device, a power source in electrical communication with the electrical signal generator, and the signal activator, where the signal activator is configured to activate in response to receipt of a communication with the activation device by the antenna and the electrical signal generator configured to generate one or more electrical stimuli in response to activation by the signal activator, and the electrical stimuli configured to stimulate one or more nerves of a user wearing patch 110 at least at one location proximate to patch 110. Additional details of examples of patch 110 are disclosed in U.S. Pat. No. 10,016,600, entitled "Topical Neurological Stimulation", the disclosure of which is hereby incorporated by reference.

Figure 2:
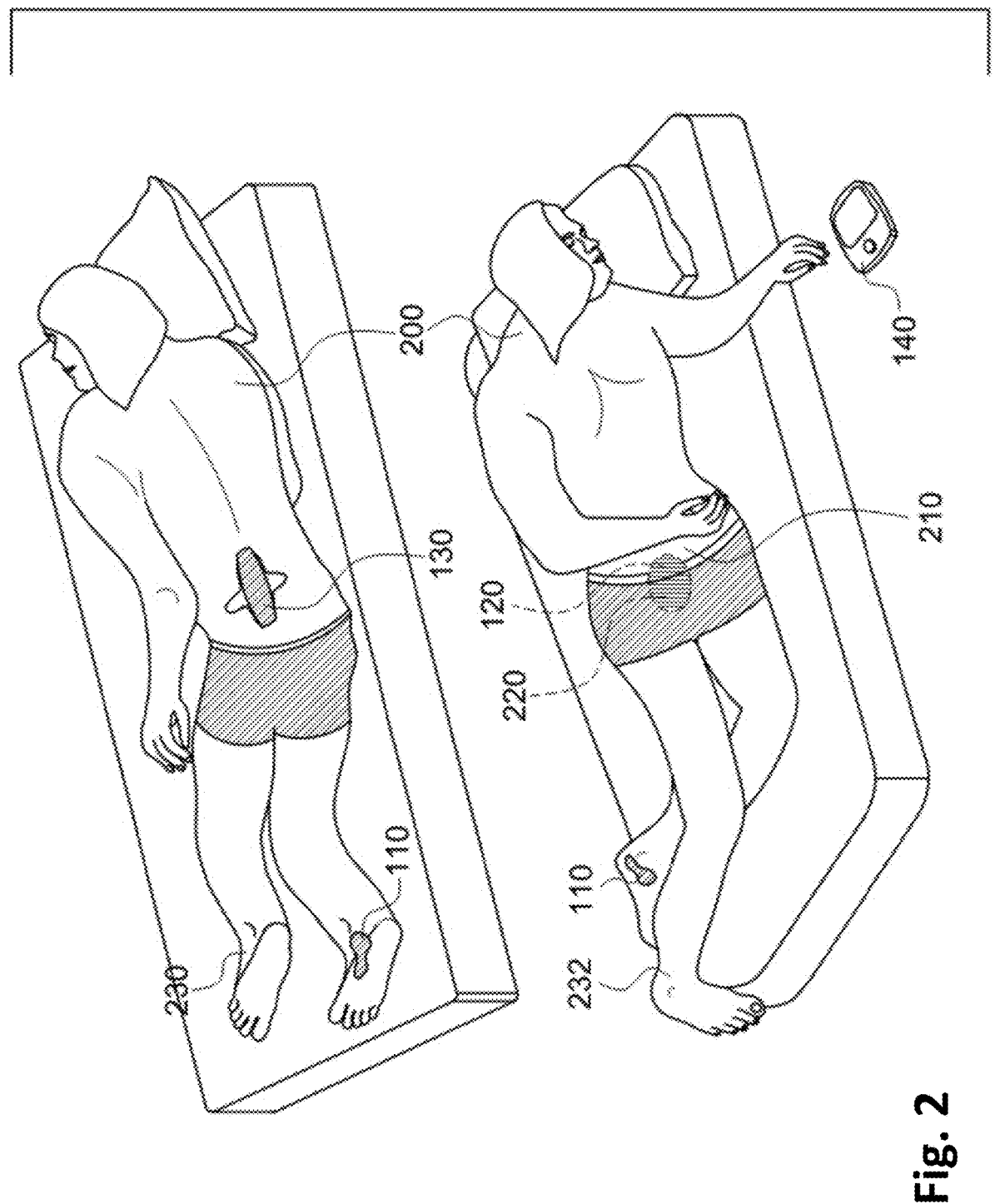
FIG. 2 illustrates a user using an example nocturia reduction system.

FIG. 2 illustrates a user 200 using an example nocturia reduction system 100. As shown in FIG. 2, user 200 has an abdomen 210, a bladder 220, a left ankle 230 and a right ankle 232. User 200 is shown in a prone posture/state, as if sleeping.

In some examples, nocturia reduction system 100 includes patch 110 with fob 150. In other examples, system 100 includes patch 110, bladder monitoring device 120 and fob 150. The elements described in conjunction with FIG. 1 may be combined in a variety of ways to implement systems which range from user activated implementations to fully automatic, without user intervention, pre-urge stimulation.

Further to the above discussion, a significant portion of injuries among people 65 and older is from falls, and 70% of accidental deaths in people 75 and older are from falls. A significant number of those falls occur at night when the person maneuvers from bed to bathroom and back again. By reducing the number of such excursions, through the use of the inventions disclosed herein, the number of injuries can be reduced, along with complications from those injuries, some of which may lead to death.

Specifically, postponing the need to urinate may reduce the number of excursions to the bathroom. Nocturia reduction system 100 incorporates the generation of signals to patch 110 to stimulate the tibial nerve. The nerve stimulation acts to suppress the urge to urinate. Analysis has shown that repeated stimulation of the tibial nerve has effects on the micturition urge for shorter and shorter periods of time, until eventually the stimulation of the tibial nerve has no effect on the urge. The urge then cannot be overcome by further stimulation and then the user must act on this urge by voiding their bladder. The times between urges may lengthen as the bladder nerves adapt to repeated stimulations, and this may reduce the number of excursions to the bathroom as well, resulting in a plasticity effect.

Figure 3A:
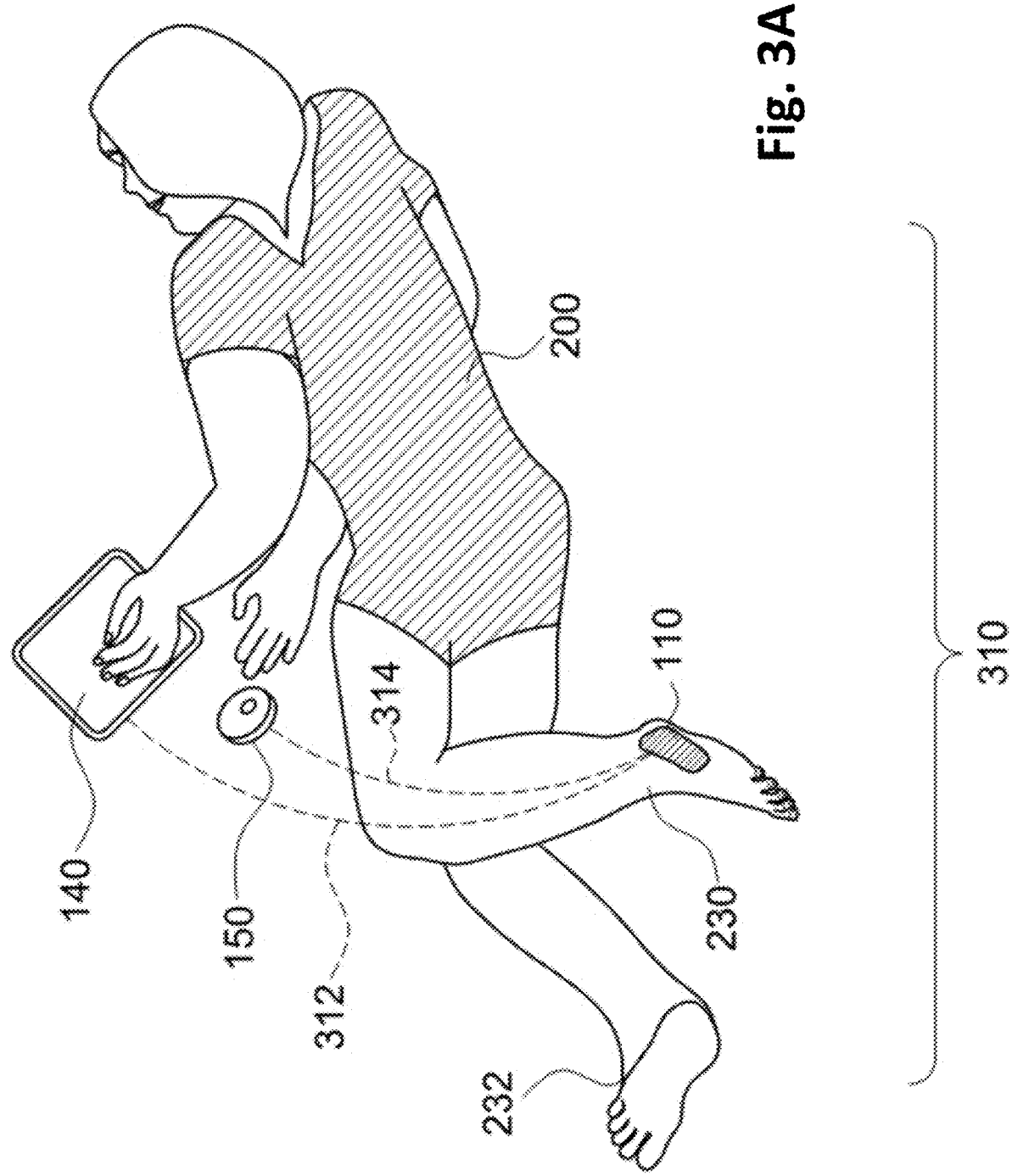
FIG. 3A illustrates a user using an example nocturia reduction system.

FIG. 3A illustrates a user 200 using an example nocturia reduction system 310. System 310 includes patch 110, and a smart controller 140, such as a smartphone or tablet, or fob 150. User 200 may indicate to smart controller 140 or fob 150 directly through a user interaction when the user is beginning a "sleep period" and again when the user is ending a sleep period. The designation of a sleep period can also be determined by other external signals such as time of day, location of the user, amount of activity, posture, and other signals. During the sleep period, when the user senses an urge to urinate, the user then indicates through a button or similar user interaction on smart controller 140 or fob 150 that the urge is to be suppressed. Smart controller 140 or fob 150 then signals, via signal 312 or 314, respectively, to patch 110. Patch 110 then stimulates, via external electrodes, the tibial nerve in the left ankle 230 or the right ankle 232, and the urge is suppressed for a period of time.

Figure 3B:
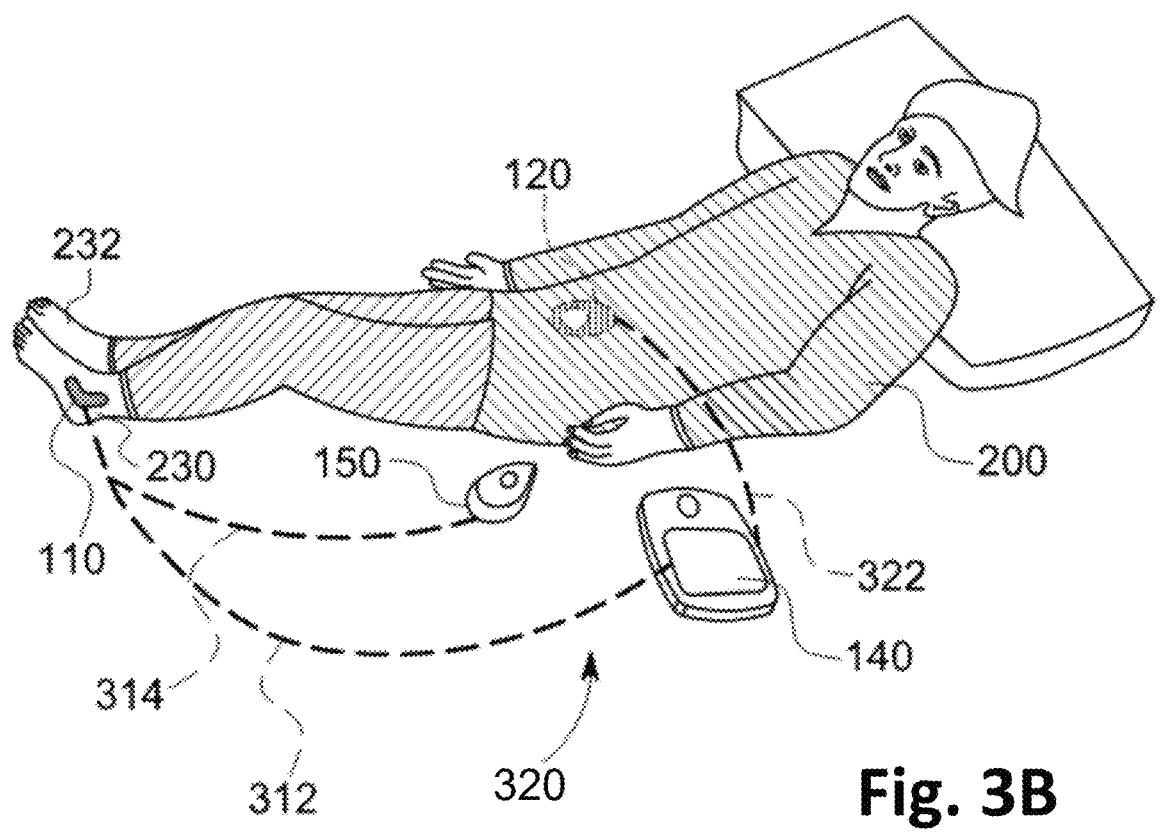
FIG. 3B illustrates a user using an example nocturia reduction system.

FIG. 3B illustrates a user 200 using an example nocturia reduction system 320. System 320 includes patch 110, bladder monitoring device 120, and smart controller 140 or fob 150. During the sleep period, when bladder monitoring device 120 anticipates that the user may experience an urge to urinate, bladder monitoring device 120 signals 322 to smart controller 140 or fob 150 to notify user 200. Smart controller 140 or fob 150 signals user 200, using for example an audible or visual annunciator, that an urge to urinate is expected. If user 200 indicates through a button or similar interface on smart controller 140 or fob 150 that the urge be suppressed, then smart controller 140 or fob 150 signals, via signal 312 or 314, respectively, to patch 110. Patch 110 then stimulates, via external electrodes, the tibial nerve in the left ankle 230 or the right ankle 232, and the urge is suppressed for a period of time.

Figure 3C:
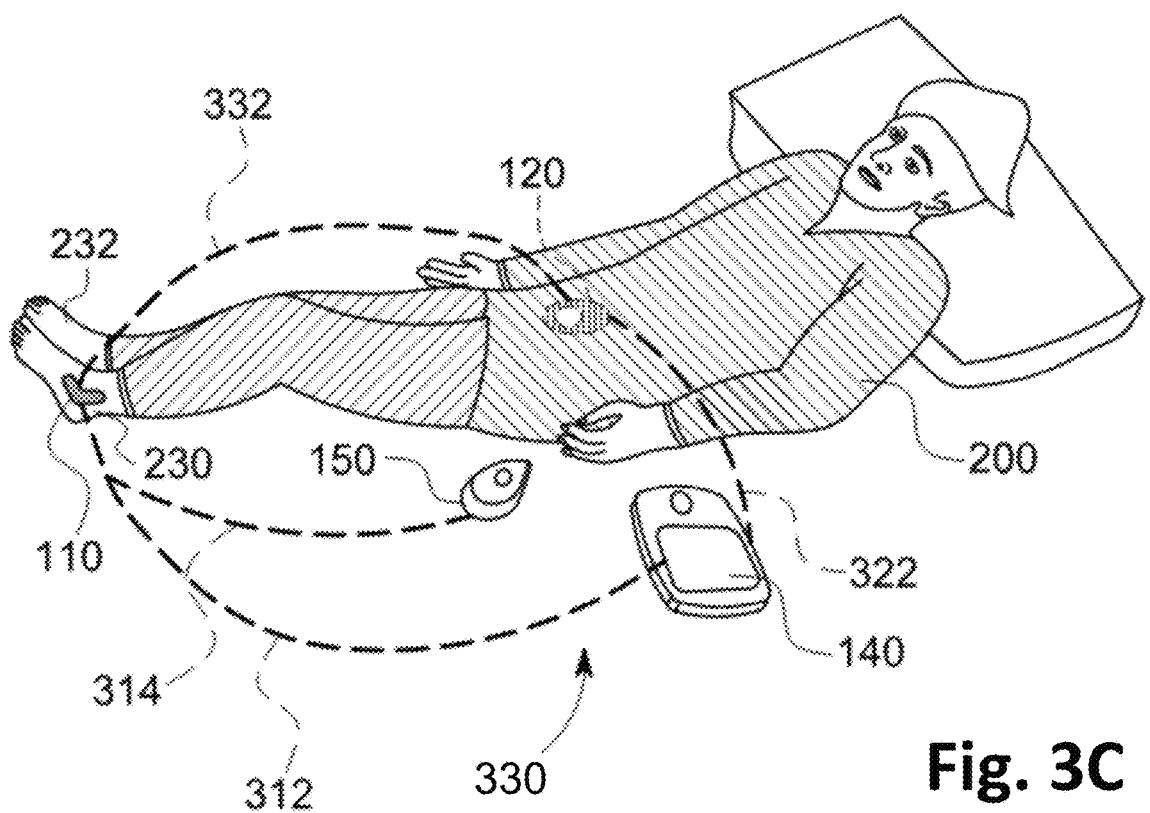
FIG. 3C illustrates a user using an example nocturia reduction system.

FIG. 3C illustrates a user 200 using an example nocturia reduction system 330. System 330 includes patch 110, bladder monitoring device 120, and smart controller 140 or fob 150. During the sleep period, when bladder monitoring device 120 anticipates that the user may experience an urge to urinate, bladder monitoring device 120 signals patch 110 via signal 332, and patch 110 then stimulates, via external electrodes, the tibial nerve in the left ankle 230 or the right ankle 232, and the urge is suppressed for a period of time, thus preventing the user from waking up.

Figure 3D:
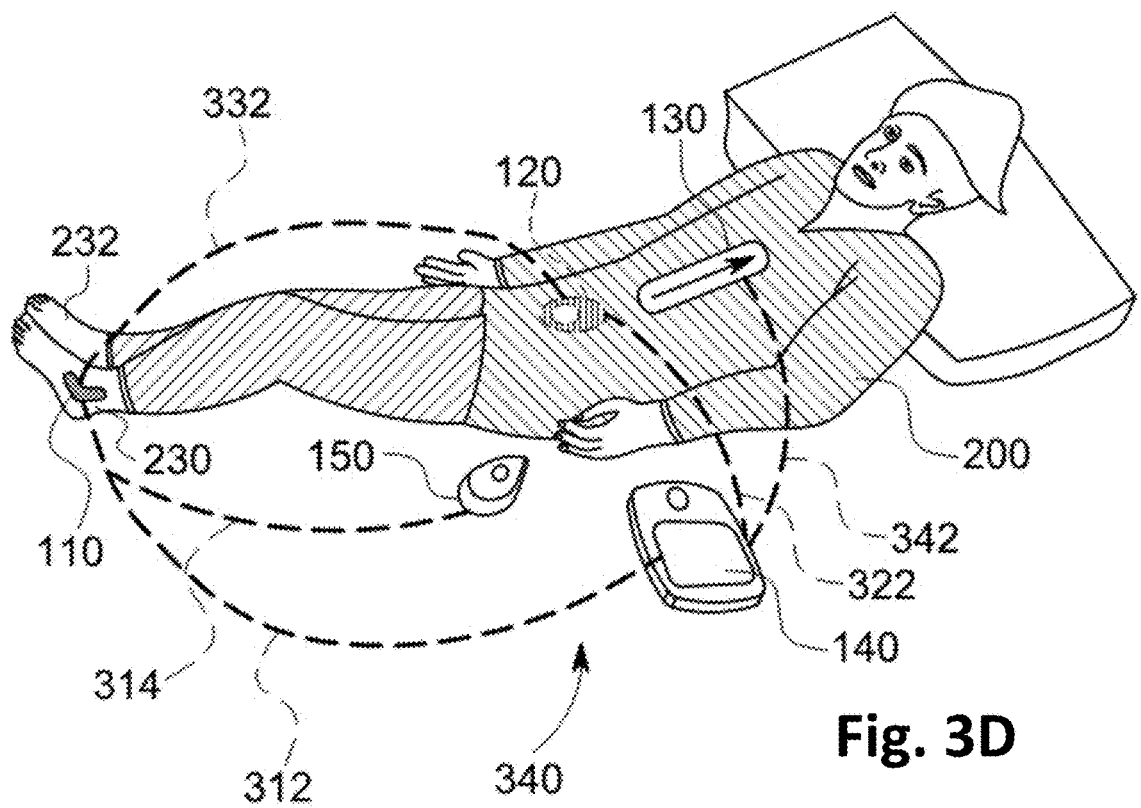
FIG. 3D illustrates a user using an example nocturia reduction system.

FIG. 3D illustrates a user 200 using an example nocturia reduction system 340. System 340 includes patch 110, bladder monitoring device 120, posture indication device 130 and smart controller 140 or fob 150. Posture indication device 130 determines through postural measurements when the user is beginning a sleep period and when the user is ending a sleep period and then signals via signal 342 the determination to smart controller 140. During the sleep period, when bladder monitoring device 120 anticipates that the user may experience an urge to urinate, bladder monitoring device 120 signals via 322 to smart controller 140 or fob 150. Smart controller 140 or fob 150 then signals, via signal 312 or 314, respectively, to patch 110 and patch 110 stimulates, via external electrodes, the tibial nerve in the left ankle 230 or the right ankle 232, and the urge is suppressed for a period of time. User input is not needed for system 340, other than for the user to opt in to the system.

In some examples of system 340, bladder monitoring device 120 may signal directly to patch 110 to suppress the urge to urinate via signal 332, thus bypassing smart controller 140.

In some examples, patch 110 stimulates the tibial nerve to elicit a suppressive nerve response, which, in turn, suppresses the urination impulse.

In some examples, bladder monitoring device 120 measures the state of the user's bladder 220 to determine the degree of urgency in voiding bladder 220. In some examples, bladder monitoring device 120 uses ultrasound to measure the state of bladder 220.

In some examples, bladder monitoring device 120 may measure other biometric attributes of user 200 to determine the degree of urgency in voiding bladder 220. Examples of these measurements may be a clenching of abdominal muscles, or restlessness during sleep, or the shape or opacity of the bladder when imaged.

Biometrics refers to body measurements and calculations and metrics related to human characteristics. Biometric identifiers are the distinctive, measurable characteristics used to label and describe individuals and include physiological and behavioral characteristics. Physiological characteristics are related to the shape of the body. Examples include veins, face recognition, DNA, palm print, hand geometry, iris recognition, retina and odor/scent. Behavioral characteristics are related to the pattern of behavior of a person, including typing rhythm, gait, and voice.

In some examples, bladder monitoring device 120 measurements are correlated to "empty", "partially-full", and "full" bladder states by interaction between user 200, and one or both of smart controller 140 and fob 150.

Figure 4:
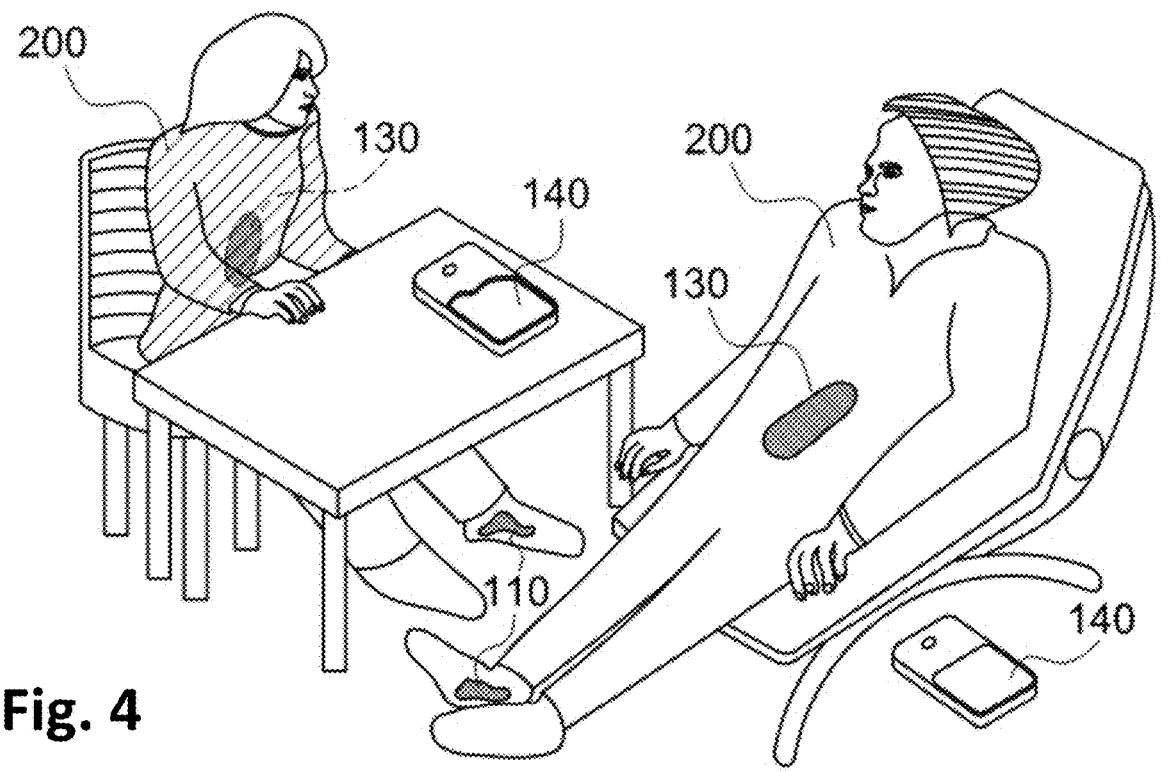
FIG. 4 illustrates a user with a posture indication device secured to the user's body.

FIG. 4 illustrates user 200 with posture indication device 130 secured to user 200 on the surface of the abdomen, with alignment mark 134 (not shown on FIG. 4) aligned vertically on the user's body. The signal value sent from posture indication device 130 to one or both of patch 110 and smart controller 140 is a member of a set of signal values for which each signal value is interpreted uniquely by patch 110 or smart controller 140, or both, to be an indication of the user's prone versus non-prone posture/state. For example, one signal value may correspond to a prone position, a second signal value may correspond to a reclining position, a third signal value may correspond to a seated position, and a fourth signal value may correspond to a standing position (not shown in FIG. 4).

In some examples, posture indication device 130 provides one measurement value when the user is in the prone posture; and a second, distinct measurement value for all non-prone user postures, and functions as a sleep detection device.

In some examples, the prone position of user 200 is determined without the use of posture indication device 130, such as through the use of GPS, an accelerometer and other sensors that can be incorporated in other devices such as bladder monitoring device 120. The data from these elements can be analyzed to determine the prone position. For example, the location of smart controller 140 or fob 150, or both, at the bedside or in the bed for longer than a pre-set time limit may be used as an indicator that user 200 is in the bed and in a prone position.

In some examples, user 200 indicates explicitly their position as either prone or non-prone on smart controller 140 through interaction with display 142 (e.g., a touchscreen) or acknowledgment button 144, or through interaction with fob 150, or other means. When smart controller 140 is informed of the user's prone position, such as at bedtime, smart controller 140 places patch 110 and bladder monitoring device 120 into a state of monitoring urination urges. When smart controller 140 is informed of the user's non-prone position, such as during daylight activities, smart controller 140 places patch 110 and bladder monitoring device 120 into a state of standby, thereby no longer monitoring bladder states.

In some examples, when user 200 indicates explicitly their position to smart controller 140, posture indication device 130 is not used.

In some examples, a first patch 110 is located on left ankle 230 and a second patch 110 is located on right ankle 232. Smart controller 140 can use the two patches 110 to analyze location data and determine the position of user 200.

In some examples, user 200 uses fob 150 to send data and control information to smart controller 140. In some examples, user 200 uses smart controller 140 directly, and fob 150 is not used. In some examples, fob 150 communicates data and controls with smart controller 140 through wireless means.

In some examples, user 200 does not wear patch 110, or bladder monitoring device 120, or both, when in the non-prone or waking state.

In some examples, analysis of bladder monitoring device 120 measurements and posture indication device 130 measurements are performed by one or both of patch 110 and smart controller 140, or by any other available processor of system 100.

In some examples, the communication of data and control among the smart controller 140, patch 110, bladder monitoring device 120 and posture indication device 130 may be by wireless means through the use of Bluetooth Low Energy ("BLE"), Wi-Fi, or other means. In some examples, the communication of data and control between bladder monitoring device 120 and posture indication device 130 may be by wired means.

In some examples, bladder monitoring device 120 and posture indication device 130 may be combined into one unit with a common processor and common power source, data and control between bladder monitoring device 120 and posture indication device 130 being in this case through wired or wireless means. This combined unit may communicate data and control with smart controller 140 and patch 110 through wireless means.

In some examples, bladder monitoring device 120 and posture indication device 130 and smart controller 140 may be combined into one unit with a common processor and common power source, data and control between bladder monitoring device 120, posture indication device 130 and smart controller 140 being in this case through wired or wireless means. This combined unit may communicate data and control with patch 110 through wireless means.

The power sources of patch 110, bladder monitoring device 120, posture indication device 130, smart controller 140 and fob 150 may be powered by battery or rechargeable means, including movement based kinetic energy, solar or other alternative energy.

In some examples, user 200 indicates to smart controller 140 the level of pressure they experience in bladder 220 (i.e., the degree of urge to urinate). Smart controller 140, through analysis of repeated inputs from the user, matches the measurements of the bladder from bladder monitoring device 120 to the user's degree of urge to urinate, such that smart controller 140 may, using only bladder monitoring device 120 measurements and the smart controller's own analysis, anticipate the user's degree of urge to urinate. This repetition of user input to smart controller 140 serves to calibrate the smart controller's response to measurements from bladder monitoring device 120.

In some examples, analysis of measurements from one or both of smart controller 140 and bladder monitoring device 120 may be performed by processing in a remote server, in the cloud, or on a computer separate from smart controller 140 but local to the user, such as a local server.

Further, artificial intelligence and machine learning may be implemented in order to perform analysis of when an individual may have an urge to urinate. The inputted data used to train a machine learning algorithm, such as linear regression, clustering, or a neural network, in order to generate a trained model, can be a history of an individual's sleep patterns over an extended period of time. Further, many users' data can be uploaded to the cloud and the history of a large population can be analyzed. Machine learning pattern matching can be used to match a user to accumulated data for parameters for the user, such as the user's age, sex, type of medicine being used, or any other relevant data.

User 200 may choose to allow the "automatic mode" (thereby opting in to the feature), or to allow only the "basic" or "semi-automatic" modes, or both (thereby opting out of the "automatic mode" feature).

In some examples, in "semi-automatic mode" or "automatic mode", patch 110 sends an activation signal (i.e., electrical stimulation), via external electrodes, to the tibial nerve in the user's left ankle 230 or right ankle 232 and repeats this signal according to a timer preset by user 200. The interval between activations is selected to effectively postpone the urge to urinate according to the user's preference.

In some examples, nocturia reduction system 100 measures the user's sleep schedule over a period of days or weeks or longer, noting the clock time when the user begins the sleep period and the clock time when the user wakes during or at the end of the sleep period. System 100 analyzes this data and determines the most effective clock times to wake user 200, assuming that when the user is in the sleep period they are asleep. The system thereby wakes the user at times more suited to preserving effective sleep instead of the times of the user's own urges to urinate, while also providing sufficient waking times for the user to wake, go to the toilet, void the bladder, and return to sleep, all without wetting or soiling the bed or bedclothes.

System 100 can wake the user multiple ways, including using an audible or visual annunciator that is part of smart controller 140. In some instances, the activation of the electrodes of patch 110 may be used to wake up the user if the level of charge that is applied is high enough to generate some electrical discomfort. However, for most example implementations, the activation of the electrodes of patch 110 actually prevents the user from waking up by delaying an urge to urinate that would ordinarily wake up the user.

Figure 5:
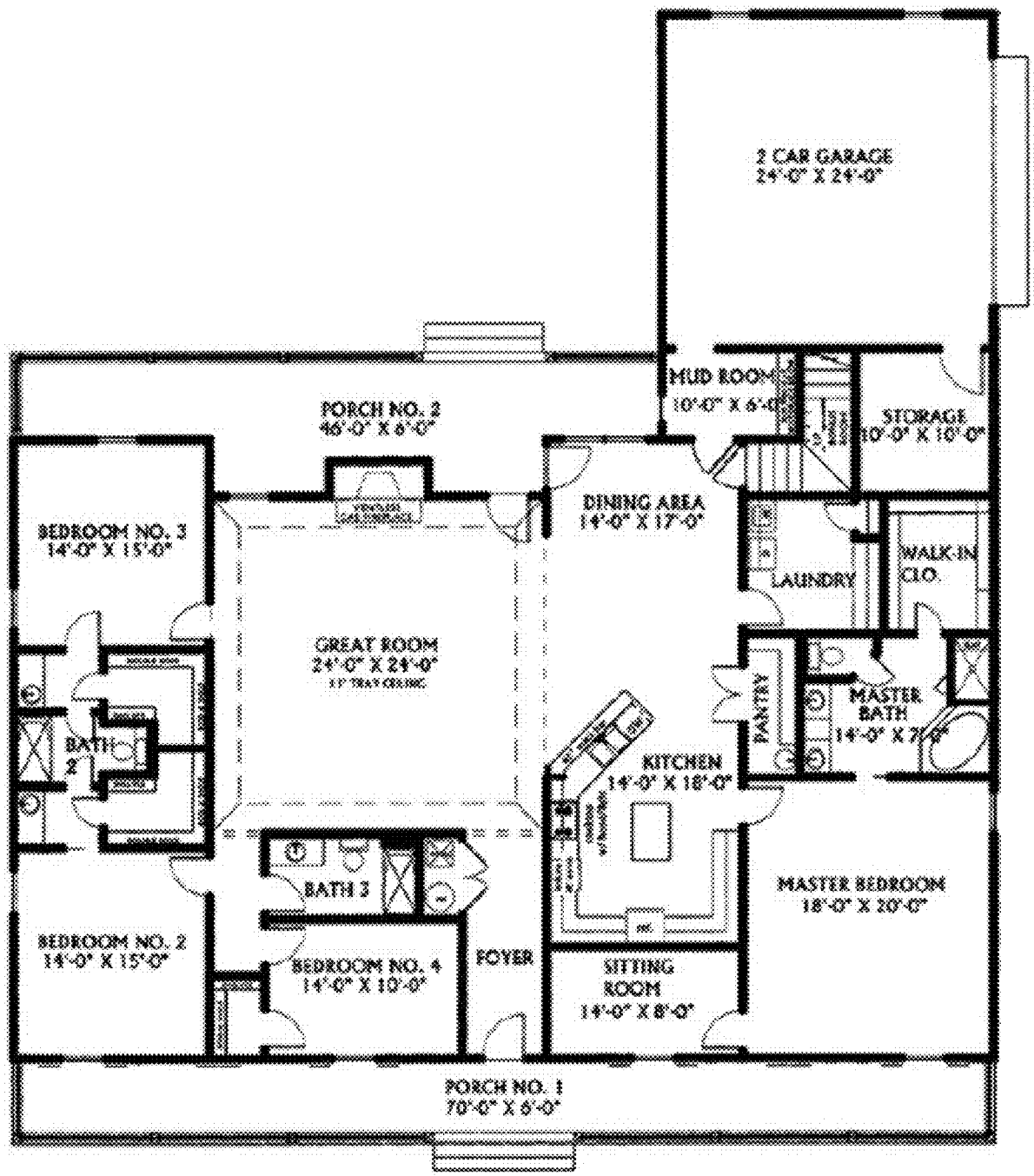
FIG. 5 illustrates several paths from bed to bath and toilet to show that there may be a variety of obstacles and opportunities for injury along each route.

FIG. 5 illustrates several paths from bed to bath and toilet to show that there may be a variety of obstacles and opportunities for injury along each route. From the Master Bedroom to the Master Bath, the user must not only pass through the door to the bathroom, but also through a second door to the toilet. Bedroom #2 and #2 lead through two doorways each to Bath #2. Bedroom #4 to Bath #3 includes a hallway. Any of these paths may be made more complex by objects on the floors, threshold steps and the need to enable lights.

In some examples, in "semi-automatic mode" or "automatic mode", nocturia reduction system 100 sends the suppressing signal to patch 110 or sends a warning message to the user with sufficient lead time before it anticipates an urge to urinate that user 200 will have sufficient time to wake, navigate to the toilet along routes such as those in FIG. 5, and be ready to urinate, thus reducing the risk of soiling the bed clothes or night clothes.

In some examples, nocturia reduction system 100, with or without posture indication device 130, determines that user 200 has moved to a non-prone position, and smart controller 140 then sends signals to lighting fixtures on the user's route from the bed to the toilet, thereby reducing the risk of falls in the dark. This process of controlling lighting may be enhanced to account for the time of day or degree of darkness in the rooms, or both, such that the lighting activations occur only when the existing level of illumination is insufficient for the user when they move from bed to toilet and back to bed.

In some examples, nocturia reduction system 100, with or without the posture indication device 130, determines that the user 200 has moved to a non-prone position, and smart controller 140 then sends signals to the user's bed to adjust the position of the bed to facilitate the user's egress from bed to floor.

Figure 6:
FIG. 6 illustrates the phases of the sleep cycle.

It is known that sleep is particularly recuperative during certain phases of a person's sleep period. FIG. 6 illustrates the phases of the sleep cycle. A personal device, or "sleep stage monitoring device" or sleep detection device, which may be part of nocturia reduction system 100, may monitor these phases, such that the start and duration may be measured for a Slow Wave Sleep ("SWS") period, also known as "deep sleep", and a rapid eye movement ("REM") period, where dreams occur. During SWS or REM periods, examples of the invention are used to defer urges to urinate, thereby reducing or avoiding the interruptions to sleep during these critical periods of sleep. It is known that awakening an individual from a deep sleep, Stages 3 and 4, or during REM sleep, can lead to disorientation upon awakening and increased risk of falls.

In some examples, the sleep stage monitoring device, or smart controller 140 using, for example, the microphone, measures the user's sleep cycle. The stage of sleep is signaled to smart controller 140 when the user enters and exits deep sleep or REM sleep. With this information, and coordinating with measured urination urges, smart controller 140 suppresses the urge to urinate when the user is in deep sleep or REM sleep. By monitoring both sleep cycle and urination urges, nocturia reduction system 100 reduces the number of interruptions to sleep during deep sleep and REM sleep periods.

Figure 7:
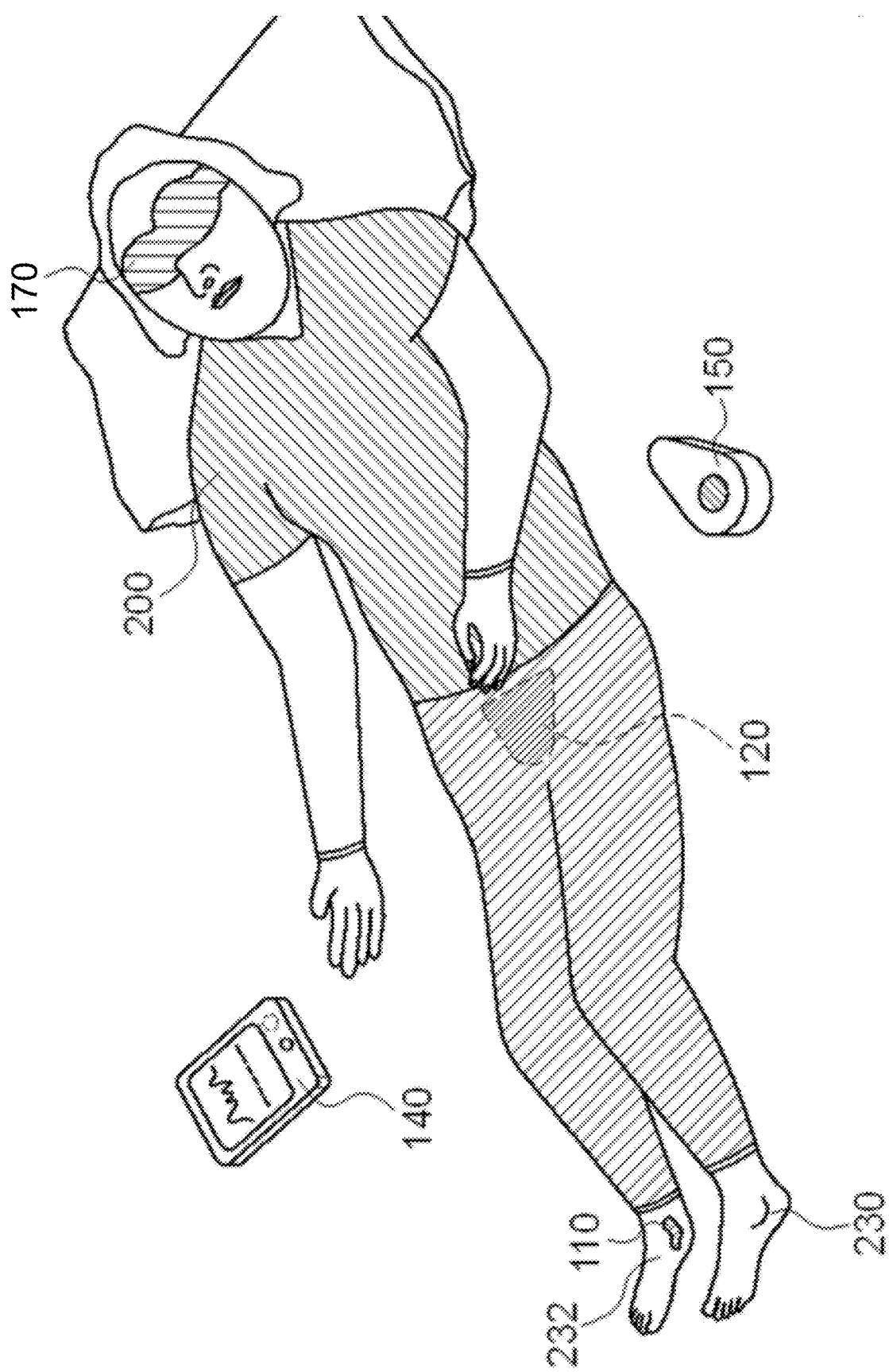
FIG. 7 illustrates another example of a user using an example nocturia reduction system.

FIG. 7 illustrates another example of a user 200 using nocturia reduction system 100. In FIG. 7, user 200 wears patch 110 on the medial left ankle 230 or on the medial right ankle 232. User 200 wears bladder monitoring device 120 on their abdomen and a sleep stage monitoring device 170 on their eyes, as an example sleep stage measurement method. Both smart controller 140 and fob 150 are included in FIG. 7.

In some examples, sleep stage monitoring device 170 measures eye movement, using electro-oculography with an optical sensor. In some examples, sleep stage monitoring device 170 is a smart phone or tablet or is implemented with smart controller 140, with a microphone or other sensors, running a sleep cycle application, which can measure the various stages of sleep.

In some examples, sleep stage monitoring device 170 is a personal fitness device that executes software, which can measure the various stages of sleep. In some examples, sleep stage monitoring device 170 measures brain activity using electroencephalographic ("EEG") sensors, and the monitoring device is worn on the scalp. In some examples, sleep stage monitoring device 170 measures cardio activity using electrocardiographic ("ECG") sensors, and the monitoring device is worn on the chest.

Similar methods may be used to measure a person's biometrics to detect REM sleep periods. Examples can determine that the user has the urge to urinate by collecting the user's biometric data, determining when a user has an urge to urinate, correlating the user's biometric data with the urge to urinate to detect urination patterns, and creating a user profile of urination patterns based on the urination patterns. Examples further can integrate the user's medical data into the user profile.

Figure 8:
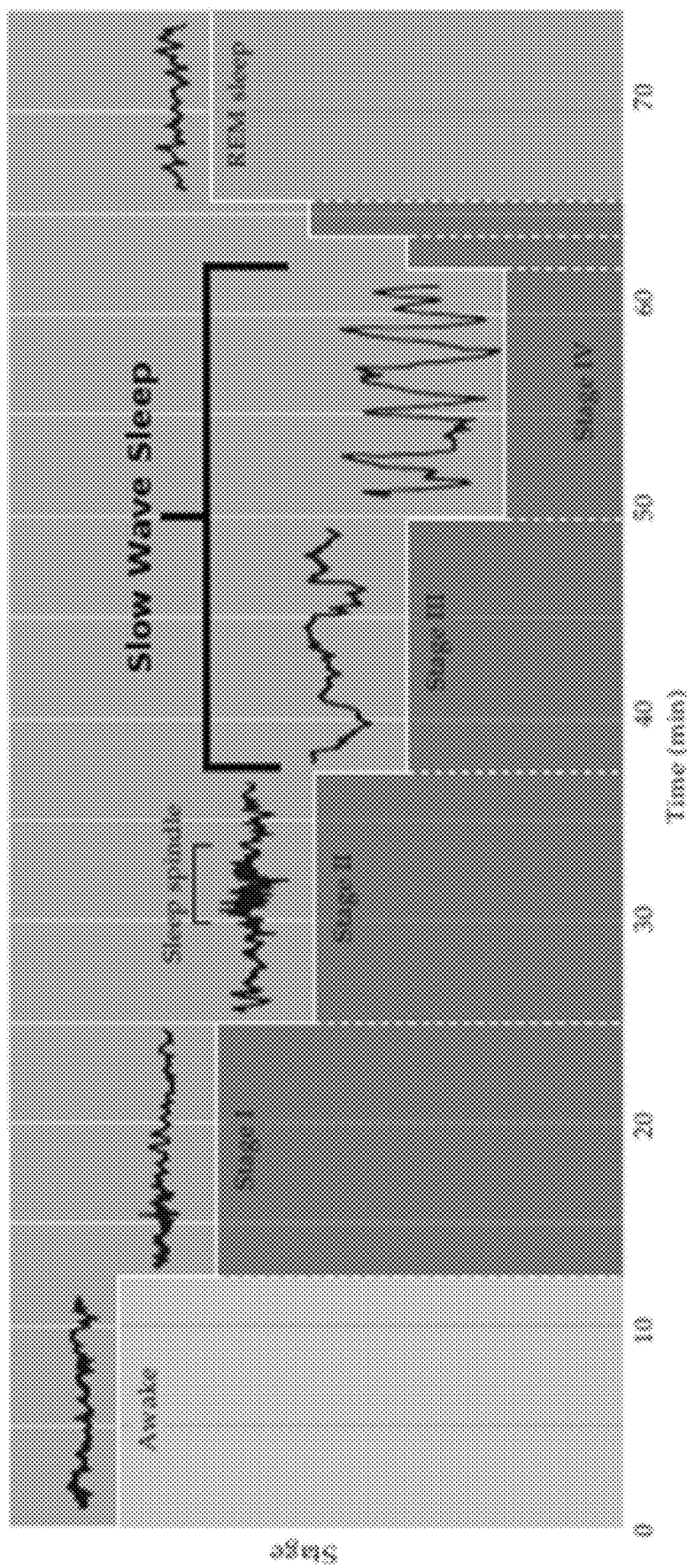
FIG. 8 further illustrates and defines the periods and stages of sleep.

FIG. 8 further illustrates and defines the periods and stages of sleep.

Figure 9:
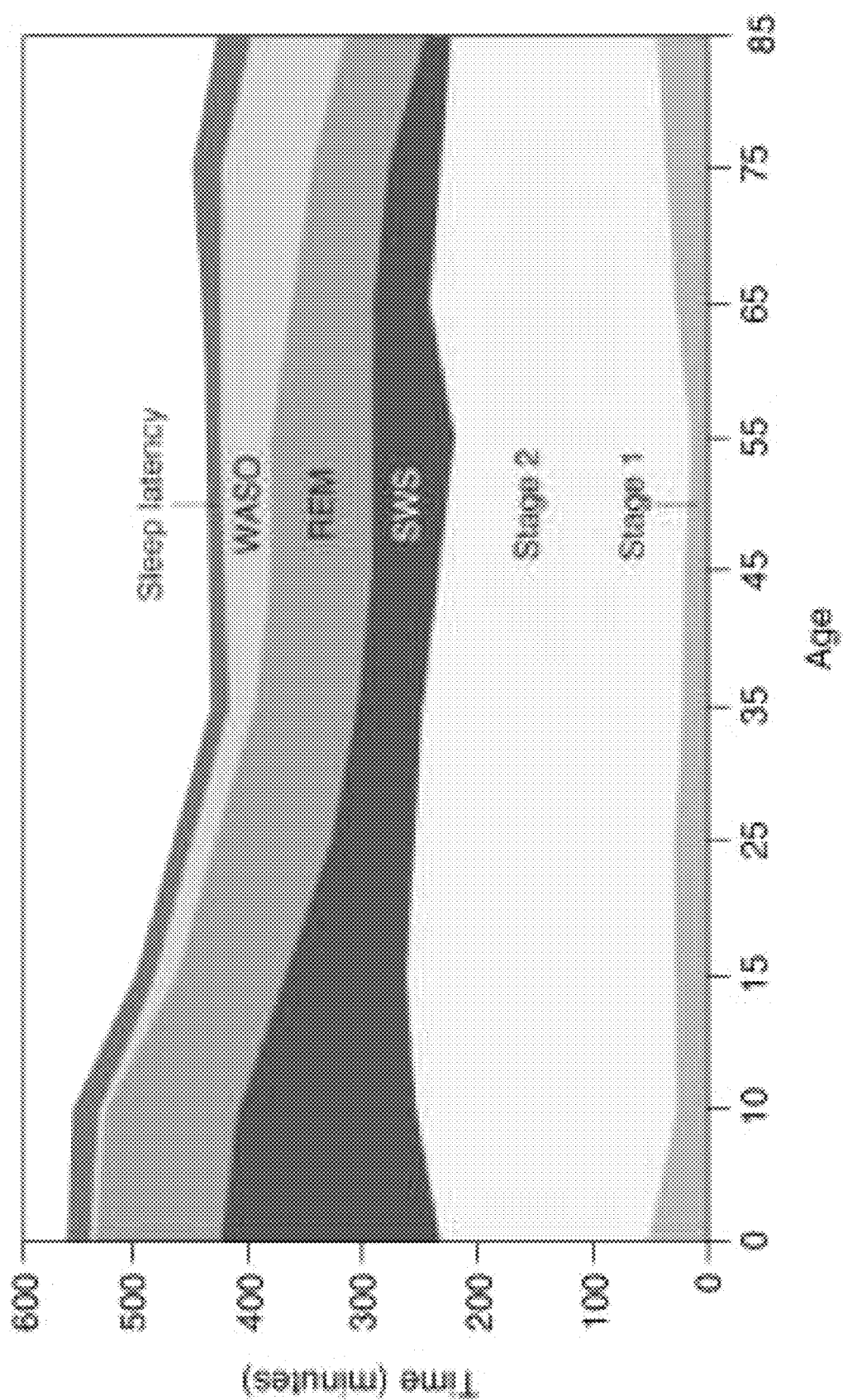
FIG. 9 illustrates how a person's sleep proceeds through several sleep cycles per night.

FIG. 9 illustrates how a person's sleep proceeds through several sleep cycles per night, for each cycle progressing through Stage 1 to 4 for NREM sleep, then to Stage 2, then to REM sleep. The percentages of sleep time in each stage and type of sleep alters as a person ages.

Figure 10:
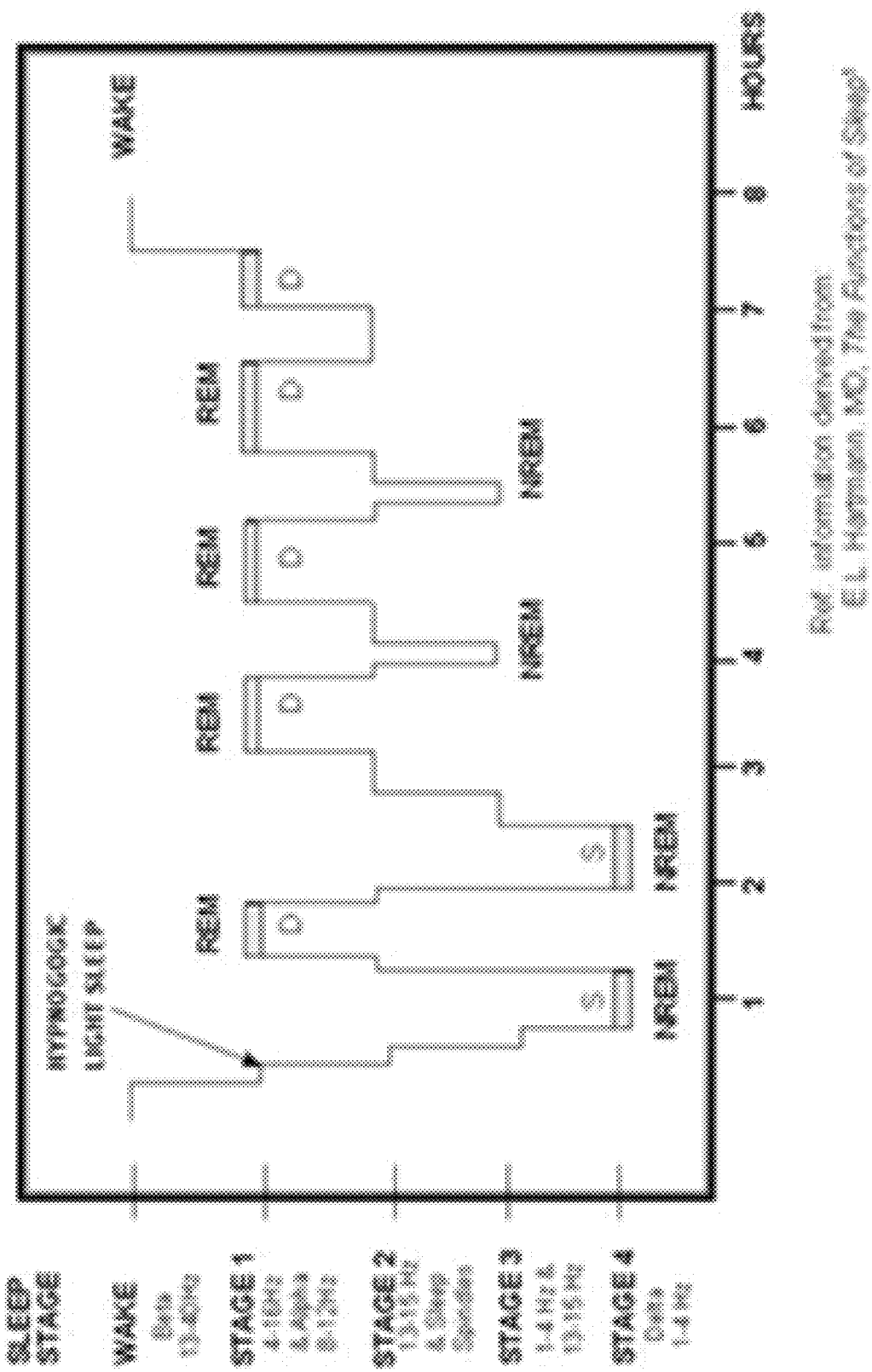
FIG. 10 illustrates how sleep patterns of young adults change as the sleep period progresses through the hours.

FIG. 10 illustrates how sleep patterns of young adults change as the sleep period progresses through the hours. The Stage 2 cycles become longer, offering more opportunity for nocturia reduction system 100 to allow urges to urinate to interrupt sleep, with less interference with SWS and REM sleep.

Figure 11:
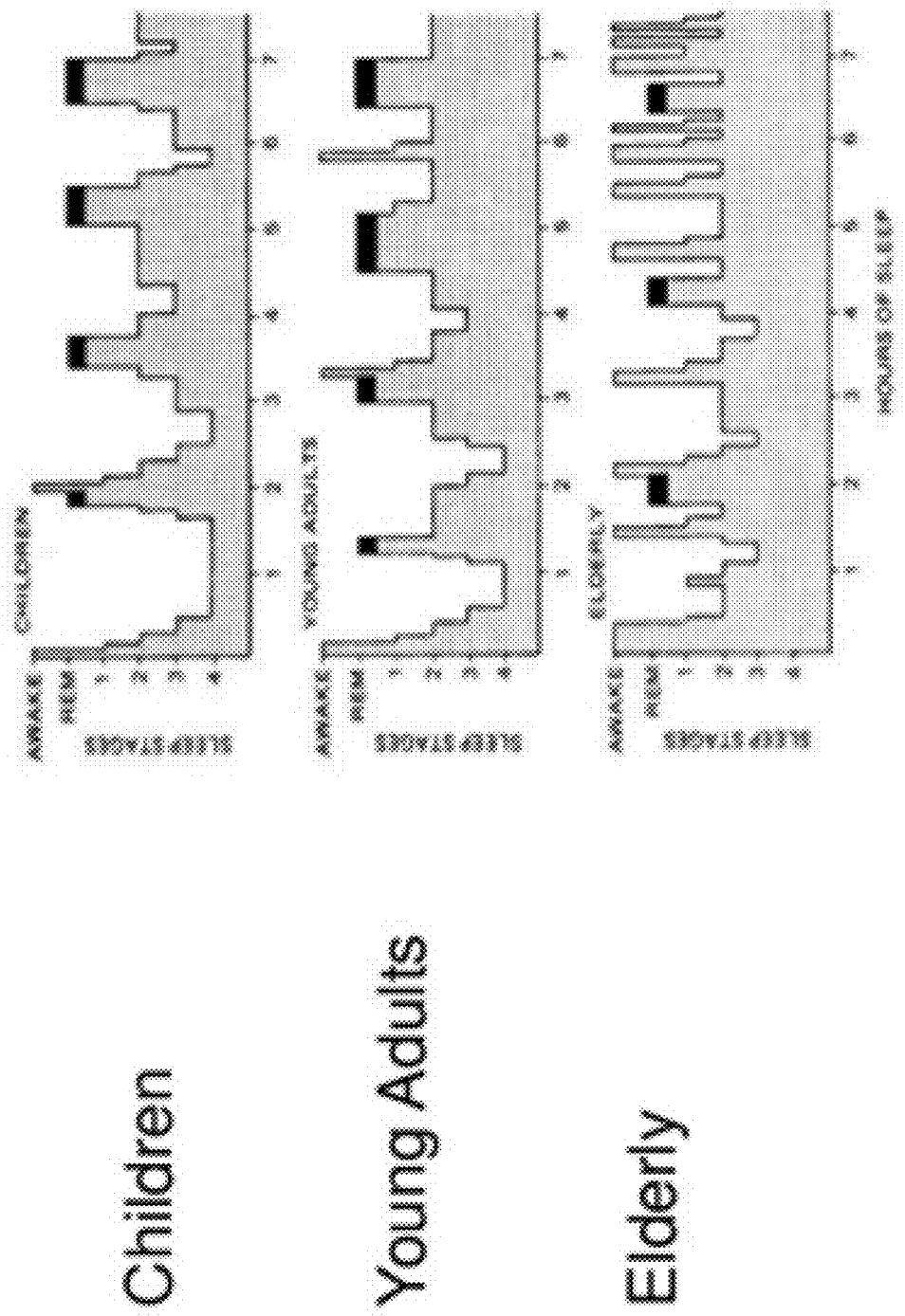
FIG. 11 illustrates how sleep patterns change with advancing age.

FIG. 11 illustrates how sleep patterns change with advancing age, showing more fractured sleep, and less time in SWS. Nocturia reduction system 100 has more opportunities to allow the urge to urinate to wake the older user, with less impact to restfulness than interruptions to SWS or REM sleep.

In some examples, nocturia reduction system 100 stimulates the user's tibial nerve at the ankle 114, using external electrodes, the stimulation counteracting the urge to urinate.

In some examples, nocturia reduction system 100, in "semi-automatic mode" or "automatic mode", measures the user's sleep cycle, moving between non-REM (NREM) and REM sleep, and the system coordinates the activation of the patch 110 to avoid waking the user during SWS periods and REM periods in order to reduce the interruptions of REM sleep caused by untimely urges to urinate.

In some examples, smart controller 140 predicts an oncoming urge to urinate through repeated recording of a user 200's nocturnal bathroom and voiding behavior, detecting specific patterns, and then applying a stimulation treatment with patch 110 at the appropriate times to postpone the urge to urinate, thereby avoiding waking the user. In this example, sleep stage monitoring device 170 and bladder monitoring device 120 are not needed.

Figure 12:
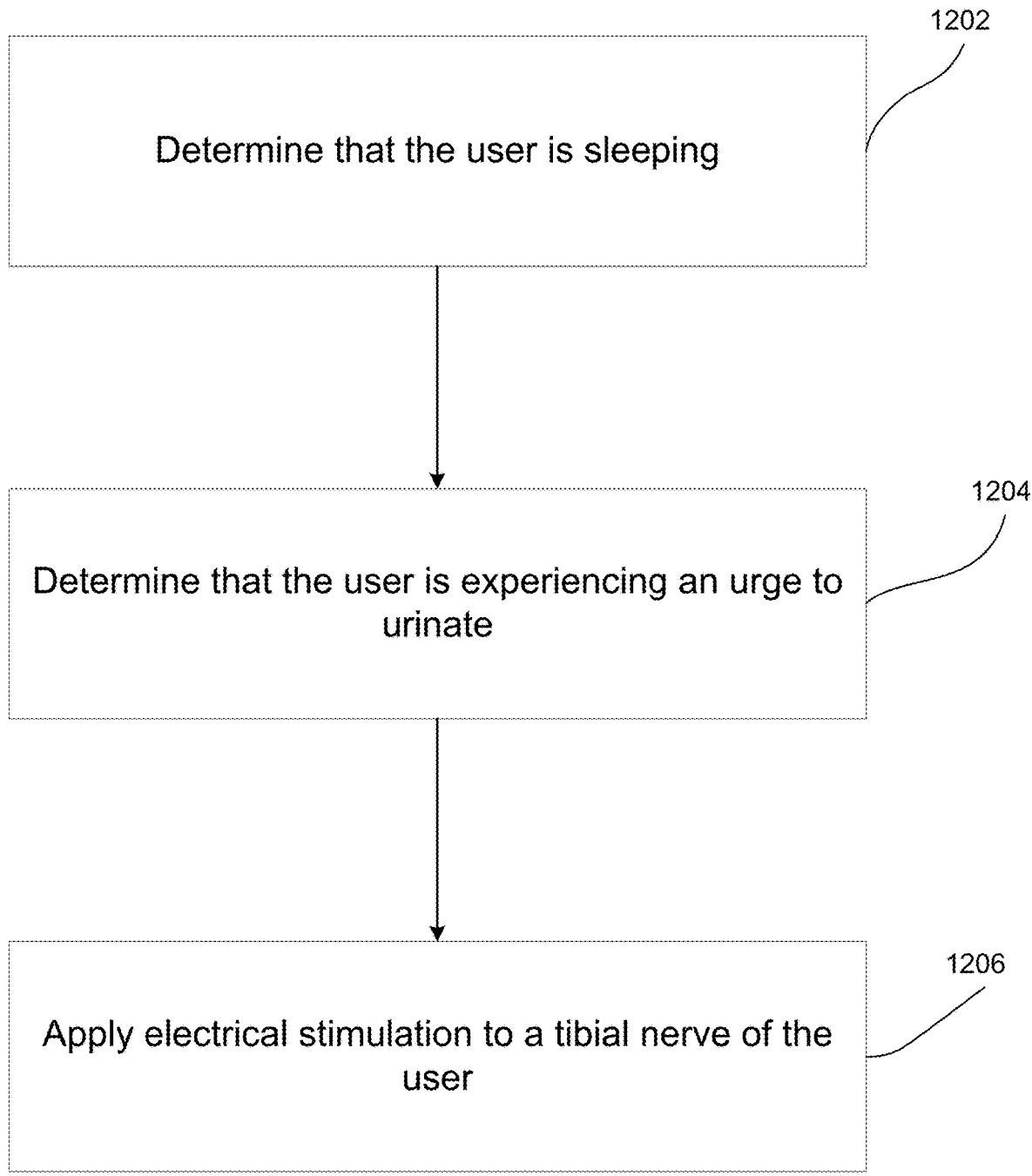
FIG. 12 is a flow diagram of the functionality of one or more of the elements FIG. 1 or 7 when reducing nocturia with example nocturia reduction systems disclosed herein.

FIG. 12 is a flow diagram of the functionality of one or more of the elements FIG. 1 or 7, such as patch 110, smart controller 140, bladder monitoring device 120, etc., when reducing nocturia with example nocturia reduction systems disclosed herein. In one example, the functionality of the flow diagram of FIG. 12 is implemented by software stored in memory or other computer readable or tangible medium, and executed by a processor. In other examples, the functionality may be performed by hardware, for example through the use of an application specific integrated circuit ("ASIC"), a programmable gate array ("PGA"), a field programmable gate array ("FPGA"), etc., or any combination of hardware and software.

At 1202, it is determined that the user is sleeping. In one example, this is automatically implemented using, for example, sleep stage monitoring device 170. In one example, the particular sleep stage is determined.

At 1204, it is determined that the user is experiencing an urge to urinate. In one example, this is automatically implemented using, for example, bladder monitoring device 120.

At 1206, an electrical stimulation, via external electrodes, is applied to a tibial nerve of the user. As a result, the urge to urinate by the user is delayed or postponed. The electrical stimulation can be repeated as needed or based on a predetermined schedule. The signal sent to patch 110 to activate the electrodes can be in response to a user manual intervention, such as interfacing with fob 150 or smart controller 140 when the user feels the need to urinate. The signal can also be generated automatically at a regularly scheduled while the user is sleeping to delay the urge to urinate. The signal can also be generated at calculated time intervals to coincide with sleep cycles, such as during REM, where it is least desirable for the user to be awoken in order to urinate.

As disclosed, examples include fob 150 communicating with patch 110, as well as other elements of FIGS. 1 and 7 communicating with each other using BLE. The elements when using BLE will undergo a pairing process. For example, fob 150 will attempt to pair with a patch 110 it detects with the strongest RSSI signal, only if the patch is within 2 feet or some other predefined distance, in the event that in the user's environment there are multiple patches 110. In other examples where a single user wears two patches 110, as disclosed above, fob 150 may pair with both patches.

After the fob pairs with a patch, that connection is "latched". The fob will pair with no other patch. The patch will pair with no other fob. Each device "remembers" the unique ID of the device with which it is paired.

If the BLE connection is broken, the fob will attempt to pair again, yet only complete a pairing with the patch it had immediately before. The fob software will not recognize other patches that may reply to the "ping" of the fob searching for its partner.

The fob pings the patch periodically as a kind of "heartbeat" to make sure that the patch is still there. Therefore, the fob knows within a margin of error that the patch is still there. This avoids the fob having to initiate a new pairing when the user presses a START button for a stimulation, such as when patch 110 provides neural stimulation. The stimulation can begin immediately, without the "5 second" delay or other predefined amount of delay needed to complete a pairing sequence. Users do not want a delay of several seconds when they press START and expect the stimulation to start right away.

If the fob detects that it has a low battery level, it saves the ID information, state and strength of the connected patch. This data is saved into nonvolatile memory in the fob. The power for the fob can then be fixed. The Fob can then immediately re-pair with the patch it used before, assumed still to be in range and on the user.

If the fob fails to pair with a patch, then the fob tries again. This is useful when a patch moves out of range of its fob. This is repeated, but the time between attempts increases slowly, to the point where the fob gives up. This saves power by reducing the number of "pings." If a ping is successful, then the fob checks the ID of that patch, and the patch checks the ID of the fob. If they are as remembered from the most recent paired condition, then the connection is reinstated.

As with pairing the fob to the patch, similar procedures can be used to pair other elements of FIGS. 1 and 7 to patch 110, or to each other.

Several examples are specifically illustrated and/or described herein. However, it will be appreciated that modifications and variations of the disclosed examples are covered by the above teachings and within the purview of the appended claims without departing from the spirit and intended scope of the invention.

What is claimed is:

1. A method of reducing nocturia for a user, the method comprising:
   affixing a patch externally on a dermis of a user adjacent to a tibial nerve of the user;
   determining that the user is sleeping during a sleep period that comprises a beginning sleep period and an ending sleep period;
   while the user is sleeping, anticipating that the user may experience an urge to urinate based on detecting a state of a bladder of the user; and
   while the user is sleeping during the sleep period and in response to anticipating that the user may experience the urge to urinate, applying external electrical stimulation to the tibial nerve of the user via the patch, the external electrical stimulation adapted to cause the anticipated urge to urinate to be suppressed and the applying comprising an initial electrical stimulation that begins only during the sleep period and only in response to the anticipation that the user may experience the urge to urinate.

2. The method of claim 1, the determining that the user is sleeping further comprises determining whether the user is in a prone state or a non-prone state, and when it is determined that the user is in the non-prone state after the beginning sleep period, automating activating lighting on a route to a toilet.

3. The method of claim 1, further comprising:
determining a sleep cycle of the user while the user is sleeping; and
applying external electrical stimulation to the tibial nerve of the user during a rapid eye movement (REM) sleep cycle or during Stages 3 and 4 sleep cycles.

4. The method of claim 1, further comprising:
determining a sleep cycle of the user while the user is sleeping; and
cancelling the application of external electrical stimulation to the tibial nerve of the user during a non-rapid eye movement (NREM) sleep cycle.

5. The method of claim 3, further comprising:
in response to anticipating that the user may experience the urge to urinate, waking up the user at a time not during the REM sleep cycle or not during the Stages 3 and 4 sleep cycles.

6. The method of claim 1, the anticipating that the user may experience the urge to urinate comprises using a machine learning model that was trained from a sleep history of a plurality of users.

7. The method of claim 1, the applying external electrical stimulation to the tibial nerve of the user is automatically activated in response to a signal from a bladder monitoring device, the patch comprising a flexible substrate, a processor directly coupled to the substrate, and electrodes directly coupled to the substrate.

8. A nocturia reduction system comprising:
a patch configured to be coupled to an ankle of a user and comprising a processor, electrodes and a communication device, the patch comprising a flexible substrate, the processor, the electrodes and the communication device directly coupled to the substrate;
a bladder monitoring device configured to determine a state of a bladder of the user while the user is sleeping to anticipate that the user may experience an urge to urinate; and
a sleep detection device configured to determine a sleep state of the user comprising determining that the user is sleeping during a sleep period that comprises a beginning sleep period and an ending sleep period;
the patch further configured to apply external electrical stimulation via the electrodes to a tibial nerve of the user in response to an activation signal while the user is sleeping during the sleep period and in response to anticipating that the user may experience the urge to urinate, the external electrical stimulation adapted to cause the anticipated urge to urinate to be suppressed and the applying comprising an initial electrical stimulation that begins only during the sleep period and only in response to the anticipation that the user may experience the urge to urinate.

9. The nocturia reduction system of claim 8, in which the determining the sleep state comprises determining whether the user is in a prone state or a non-prone state and when it is determined that the user is in the non-prone state after the beginning sleep period, automating activating lighting on a route to a toilet.

10. The nocturia reduction system of claim 8, in which the determining the sleep state comprises determining a sleep cycle of the user while the user is sleeping; and
the apply external electrical stimulation to the tibial nerve of the user configured to occur during a rapid eye movement (REM) sleep cycle or during Stages 3 and 4 sleep cycles.

11. The nocturia reduction system of claim 8, the determine the sleep state further comprises determining a sleep cycle of the user while the user is sleeping; and
cancelling the application of external electrical stimulation to the tibial nerve of the user during a non-rapid eye movement (NREM) sleep cycle.

12. The nocturia reduction system of claim 10, further comprising a wake up device configured to, in response to the anticipating that the user may experience the urge to urinate, waking up the user at a time not during the REM sleep cycle or not during the Stages 3 and 4 sleep cycles.

13. The nocturia reduction system of claim 8, the state of the bladder further comprising an urge of the user to urinate, the state determined using a machine learning model that is trained from a sleep history of a plurality of users.

14. The nocturia reduction system of claim 8, the activation signal automatically generated by the bladder monitoring device.

15. A non-transitory computer readable medium having instructions stored thereon that, when executed by one or more processors, cause the processors to reduce nocturia for a user via a patch externally affixed on a dermis of a user adjacent to a tibial nerve of the user, the reducing comprising:
determining that the user is sleeping during a sleep period that comprises a beginning sleep period and an ending sleep period;
while the user is sleeping, anticipating that the user may experience an urge to urinate based on detecting a state of a bladder of the user; and
while the user is sleeping during the sleep period and in response to anticipating that the user may experience the urge to urinate, applying external electrical stimulation to the tibial nerve of the user via the patch, the external electrical stimulation adapted to cause the anticipated urge to urinate to be suppressed and the applying comprising an initial electrical stimulation that begins only during the sleep period and only in response to the anticipation that the user may experience the urge to urinate.

16. The non-transitory computer readable medium of claim 15, the determining that the user is sleeping further comprises determining whether the user is in a prone state or a non-prone state, and when it is determined that the user is in the non-prone state after the beginning sleep period, automating activating lighting on a route to a toilet.

17. The non-transitory computer readable medium of claim 15, the reducing further comprising:
determining a sleep cycle of the user while the user is sleeping; and
applying external electrical stimulation to the tibial nerve of the user during a rapid eye movement (REM) sleep cycle or during Stages 3 and 4 sleep cycles.

18. The non-transitory computer readable medium of claim 15, the reducing further comprising:
determining a sleep cycle of the user while the user is sleeping; and
cancelling the application of external electrical stimulation to the tibial nerve of the user during a non-rapid eye movement (NREM) sleep cycle;
the patch comprising a flexible substrate, the one or more processors directly coupled to the substrate, and electrodes directly coupled to the substrate.

19. The non-transitory computer readable medium of claim 17, the reducing further comprising:
   in response to anticipating that the user may experience the urge to urinate, waking up the user at a time not during the REM sleep cycle or not during the Stages 3 and 4 sleep cycles.

20. The non-transitory computer readable medium of claim 15, the anticipating that the user may experience the urge to urinate further comprises using a machine learning model that is trained from a sleep history of a plurality of users.

21. The method of claim 1, the anticipating that the user may experience the urge to urinate comprising:
   collecting a user's biometric data;
   determining when a user has an urge to urinate;
   correlating the user's biometric data with the urge to urinate to detect urination patterns; and
   creating a user profile of urination patterns based on the urination patterns.

22. The method of claim 21, further comprising integrating a user's medical data into the user profile.

\* \* \* \* \*